United States Patent [19]

Swanson

[11] Patent Number: 5,089,023

[45] Date of Patent: Feb. 18, 1992

[54] DIFFRACTIVE/REFRACTIVE LENS IMPLANT

[75] Inventor: Gary J. Swanson, Lexington, Mass.

[73] Assignee: Massachusetts Institute of Technology, Cambridge, Mass.

[21] Appl. No.: 497,860

[22] Filed: Mar. 22, 1990

[51] Int. Cl.[5] .................................................. A61F 2/16
[52] U.S. Cl. .......................................................... 623/6
[58] Field of Search .................... 623/6, 4, 5; 351/161, 351/162

[56] References Cited

U.S. PATENT DOCUMENTS

| | | | |
|---|---|---|---|
| 4,813,955 | 3/1989 | Achatz et al. | 623/6 |
| 4,881,805 | 11/1989 | Cohen | 623/6 X |
| 4,923,296 | 5/1990 | Erickson | 623/6 X |

Primary Examiner—Ronald Frinks

[57] ABSTRACT

In an intraocular optical implant including a refractive/diffractive lens having an anterior surface and a posterior surface and a generally anterior-posterior optical axis, at least one of the surfaces has a diffractive lens profile covering about half the effective lens area of the lens. Preferably the diffractive lens profile occupies a sectoral portion of the effective lens area, as for example a semicircular sectoral portion, or a plurality of sectoral portions the sum of whose subtended angles is about 180°, as for example two sectoral portions each of whose subtended angles is about 90°.

9 Claims, 4 Drawing Sheets

DIFFRACTIVE/REFRACTIVE LENS IMPLANT

The Government has rights in this invention pursuant to contract No. F19628-85-C-0002 awarded by the Department of the Air Force.

BACKGROUND OF THE INVENTION

This invention relates to intraocular lens implants.

An intraocular lens implant can be used to partially restore the sight in an eye whose natural lens has been damaged by injury or by a disease process.

Anatomical features of the healthy human eye are shown diagramatically in FIG. 1. Light reaching the eye 10 passes first through the cornea 12, the clear front part of the outer wall 11 of the eye. The cornea is a fixed focus lens that accounts for the majority of the focal power of the eye. Behind the cornea 12 the light passes through an aqueous solution 13, termed the aqueous humor, and then through the lens 14, which further focuses the light. Behind the lens 14 the light passes through a gelatinous substance 15, termed the vitreous humor, and then it reaches the retina 16, in which the light receptors are located, on the inner surface of the wall 11 at the rear of the eye.

In a healthy eye, the natural lens is pliable, and a musculature associated with the lens can by relaxation and contraction change the shape of the lens, and particularly its thickness. Changes in the thickness of the natural lens result in changes in its focal length, allowing the lens to accommodate, that is, allowing it to focus onto the retina a clear image of objects located at various distances from the eye. The closest point on which the eye can focus, termed the "near point", can be as close as about 7 cm in a healthy young adult, and becomes greater with age or as a result of certain disease conditions.

Suspended in the aqueous humor directly anterior to the lens 14 is the iris 18, a membranous diaphragm perforated by the circular pupil 20, through which the light passes to the lens. The iris responds to varying degrees of brightness of the incident light by expanding or contracting the pupil size to allow more or less light to pass through the lens. The pupil diameter of a healthy human eye varies from about 2 mm in bright light to about 7 mm in very dim light. In optical design terminology, the iris forms the entrance pupil of the eye. The cornea 12, pupil 20, and lens 14 are aligned with their centers generally on an optical axis O—O'.

Persons suffering from cataracts gradually lose their vision as the natural lens becomes opaque to light. The cataract sufferer's vision can be restored, to a degree, by surgical removal of the damaged natural lens and replacement of it with an intraocular lens implant.

The capacity of an intraocular lens implant to restore normal vision to the eye is substantially limited by the fact that the lens implant, unlike the natural lens, has a generally fixed focal length. As described above, the healthy lens is capable of accommodation so that objects at a distance to which the person's attention is at any moment directed are at that moment sharply in focus. An intraocular lens implant is typically made from an incompressible polymeric material and its shape cannot be changed by the focusing musculature of the eye, and consequently the implant is incapable of accommodation.

An improved intraocular lens implant can be made by forming a diffractive lens profile over the entirety of the posterior or anterior surface of a refractive lens body, producing a diffractive/refractive lens. The refractive component of the lens forms a clear image onto the retina of objects located approximately at a first distance from the eye, and the diffractive component forms a clear image onto the retina of objects located approximately at a second distance from the eye. As a result, a person fitted with such a diffractive/refractive "bifocal" intraocular lens implant can see a clear image of objects located both at distances within a close range and at distances within a more distant range.

The healthy natural lens can focus effectively all the incident light onto the retina for objects at any distance at or beyond the near point. Although a diffractive/refractive lens implant is an improvement over the wholly refractive lens implant in that it provides for a focused image of either close or distant objects, it delivers substantially less than all the incident light to a focus at the retina. In known diffractive/refractive lens implants substantially less than half the incident light may be properly focused for either near or far objects, and the remaining portion of the light is not properly focused on the retina for either near or far objects, resulting in a degradation of the quality of the perceived image. Such a diffractive/refractive lens configuration may also be subject to artificial color effects, that is, distant objects may appear more blue in color than they actually are, and near objects more red.

SUMMARY OF THE INVENTION

The invention features, in one aspect, an intraocular implant that includes a refractive/diffractive lens having a diffractive lens profile covering about half the effective lens area of the lens at any natural exit pupil.

A "diffractive lens profile", as used herein, means any optical surface that focuses light by diffraction.

The "effective lens area", as used herein, means that part of the area of a plane, located at the lens and perpendicular to its optical axis, through which light passes; and the diffractive lens profile "covers about half" the effective lens area, as that term is used herein, where light passing through the diffractive lens profile passes through about half the effective lens area. The effective lens area changes as the pupil size changes, and the diffractive lens profile covers about half the effective lens "at any natural exit pupil", as that term is used herein, where light passing through the diffractive lens profile passes through about half the effective lens area, irrespective of the pupil size.

A refractive/diffractive lens configuration according to the invention, in which the diffractive lens profile covers about half the effective lens area, can bring about 50% of the incident light from objects within a more distant range and about 48% of the incident light from objects within a nearer range. Nearly all the light reaching the retina is in focus for either near-range or distant-range objects, contributing to clear image formation.

Because the diffractive lens profile covers about half the lens area at any natural exit pupil, the delivery of light is not substantially affected by the brightness of the incident light; that is, the refractive/diffractive lens configuration according to the invention brings about 50% of the incident light from more distant objects and about 48% of the incident light from nearer objects, irrespective of the pupil diameter.

In preferred embodiments, at least one surface of the refractive/diffractive lens is generally planar, the diffractive lens profile is formed on the generally planar surface of the lens, and the diffractive lens profile covers a sector of a circle whose center is on the optical axis of the lens; preferably the diffractive lens profile occupies a semicircle, and more preferably the diffractive lens profile occupies at least two sectors, each less than a semicircle, and most preferably the diffractive lens profile occupies two sectors, each of which is about a quarter circle. In preferred embodiments the diffractive lens profile is a Fresnel phase zone plate profile, more preferably configured as a blazed diffractive lens profile (most preferably as a stepped profile), and most preferably the profile has a thickness D given by $$D = \frac{\lambda_o}{\Delta n},$$

where $\lambda \cdot$ is about 550 nm.

Where the diffractive lens profile is configured as a semicircular sector of a circle whose center is at the optical axis of the lens, half the effective lens area is covered by the diffractive lens profile at any pupil size, as long as the optical axis of the lens is at the center of the pupil. More preferably, the diffractive lens profile occupies two or more sectors, subtending angles totalling 180°, so that about half the effective lens is covered by the diffractive lens profile at any pupil size even when the lens is displaced to some degree off-axis with respect to the center of the pupil, as may happen during healing and regrowth of tissues about the implant following implantation.

DESCRIPTION OF PREFERRED EMBODIMENTS

Preferred embodiments of the invention will now be described, beginning with a brief description of the drawings.

DRAWINGS

MULTIPLE-FOCUS DIFFRACTIVE LENSES

Figure 2:
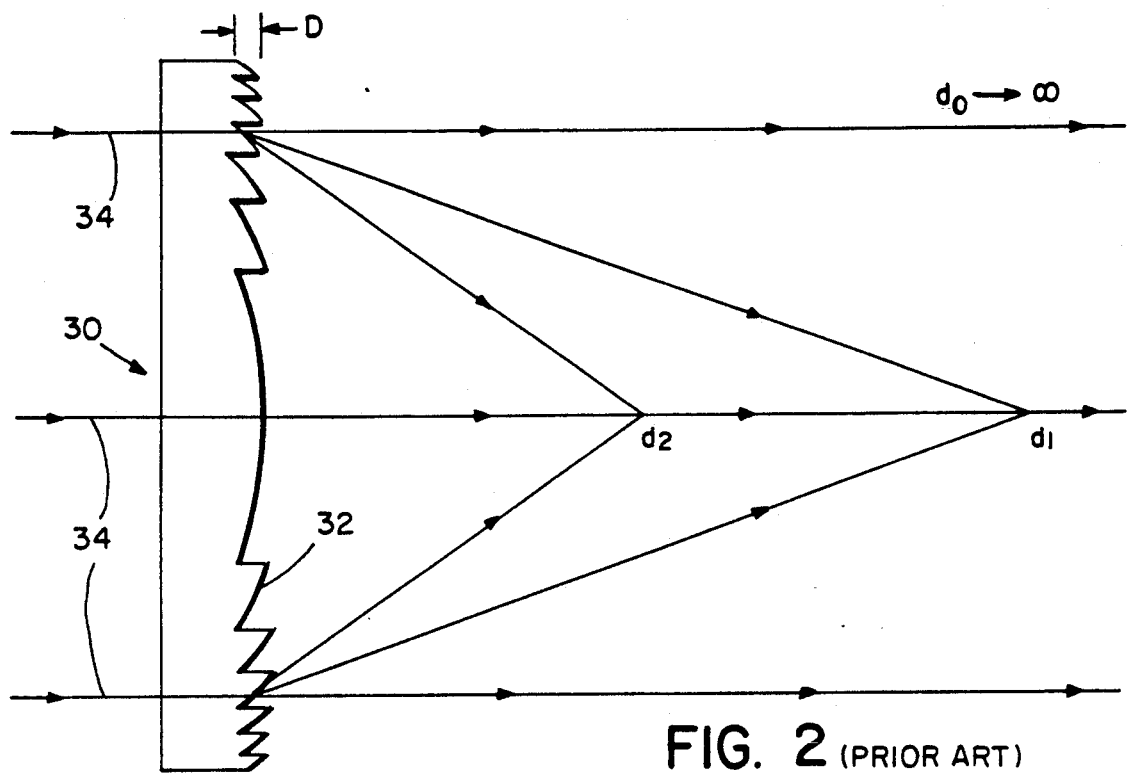
FIG. 2 is a diagram of a section through a "blazed" diffractive lens.

With reference now to FIG. 2, diffractive lens 30 is shown having a generally planar-planar configuration and having a "blazed" diffractive lens profile 32 over the entirety of its posterior surface. (The diffractive lens profile 32 is dimensionally exaggerated in FIG. 2 for illustration, and this and other Figs. herein are generally not to scale. The lens body of an intraocular lens implant for human use, for example, typically is about 5–7 mm in diameter, and the depth D of a blazed diffractive lens profile for the visible spectrum is typically on the order of a micron.) Such a diffractive lens behaves differently from a refractive lens in that the diffractive lens can have multiple focal lengths. Light of wavelength $\lambda \cdot$ that is emitted as shown for example by rays 34 from a distant object (not shown in FIG. 2), and incident on diffractive lens 30 having a focal power P, is focused at distance $d_m$, represented by $$d_m = \frac{1}{mP} \qquad (1)$$

where m is an integer.

The fractional amount of the incident light that is focused at position $d_m$ is given by $\eta_m$:

$$\eta_m = \left[ \frac{\sin\left(\pi\left[\frac{\Delta n}{\lambda} D - m\right]\right)}{\pi\left[\frac{\Delta n}{\lambda} D - m\right]} \right]^2 \qquad (2)$$

where D is the depth of the diffractive profile and $\Delta_n$ is the difference between the refractive index of the substrate and the refractive index of the surrounding medium.

According to the invention, it is desirable for an intraocular lens implant to provide a diffractive profile that equally divides all the incident light into only the two focal positions $d_0$ and $d_1$. As equation (2) shows, however, the diffractive profile can at best place 40.5% of the light at $d_0$ and 40.5% of the light at $d_1$. This condition is achieved when the depth of the diffractive lens profile is:

$$D = \frac{\lambda_o}{2\Delta n}.$$

The remaining 19% of the light, placed into different $d_m$ positions, is effectively wasted and contributes to a degradation of the image at $d_1$, that is, if the retina were located at $d_1$, the light placed into other $d_m$ positions would degrade the image on the retina.

Figure 3:
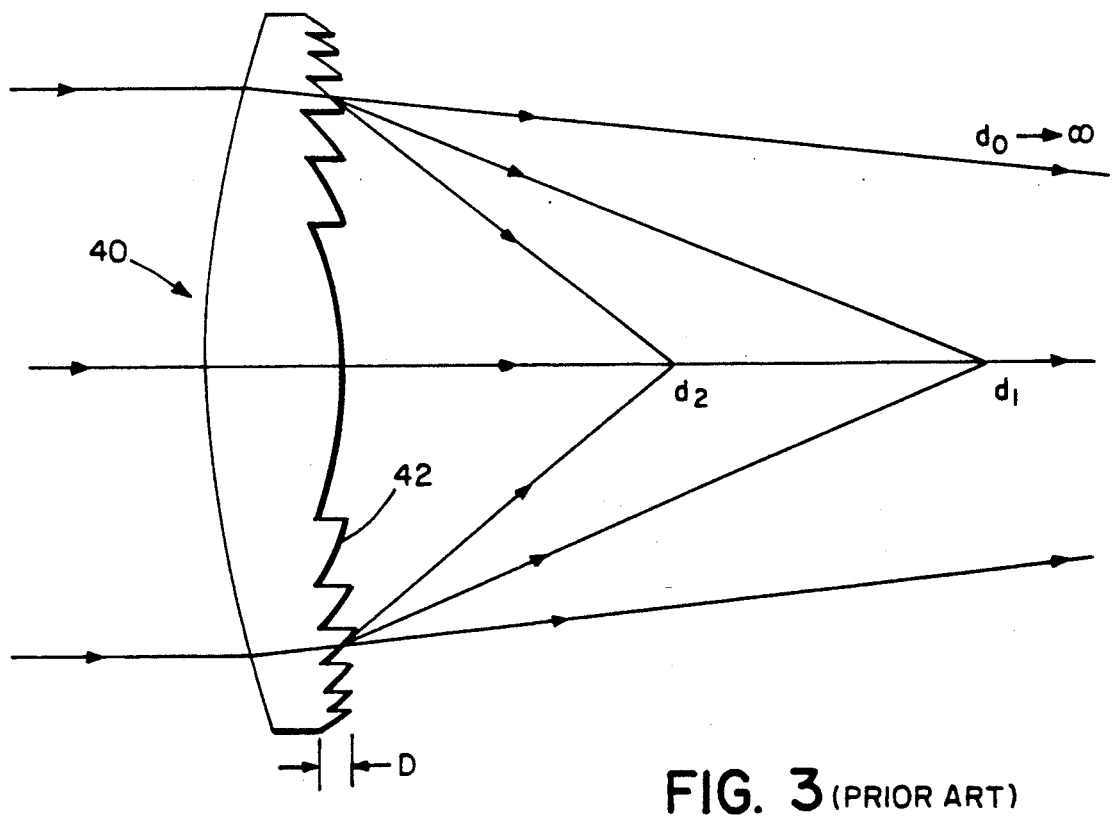
FIG. 3 is a diagram of a section through a "blazed" refractive/diffractive lens.

Such a diffractive lens profile can be placed on a surface of a refractive lens, forming a refractive/diffractive lens. With reference now for example to FIG. 3; refractive/diffractive lens 40 is shown having a generally convex-planar configuration and having a "blazed" diffractive lens profile 42 over the entirety of its posterior surface. Placing a diffractive profile on a surface of a refractive lens changes the distances $d_m$, by amounts depending upon the focal power of the refractive lens. Whatever the focal power of the refractive lens, however, the amount of light delivered to any given focal position is determined from equation (2), and light delivered to $d_m$ positions other than $d_1$ would be wasted, degrading the image on a retina located at $d_1$.

Known refractive/diffractive intraocular lens implants are configured generally as in FIG. 3, having a diffractive lens profile covering the entirety of one lens surface. Such a lens can at best place 40.5% of the incident light into each of the $d_0$ and $d_1$ positions.

We have discovered that an improved intraocular lens implant can be made by covering about half the surface of a refractive lens with a diffractive lens profile. By way of example, one embodiment is described below and shown in FIGS. 4 and 5. Such a lens is capable of placing about 50% of the light in the $d_0$ focal position, and nearly 50% of the light in the $d_1$ focal position.

STRUCTURE

Figure 4:
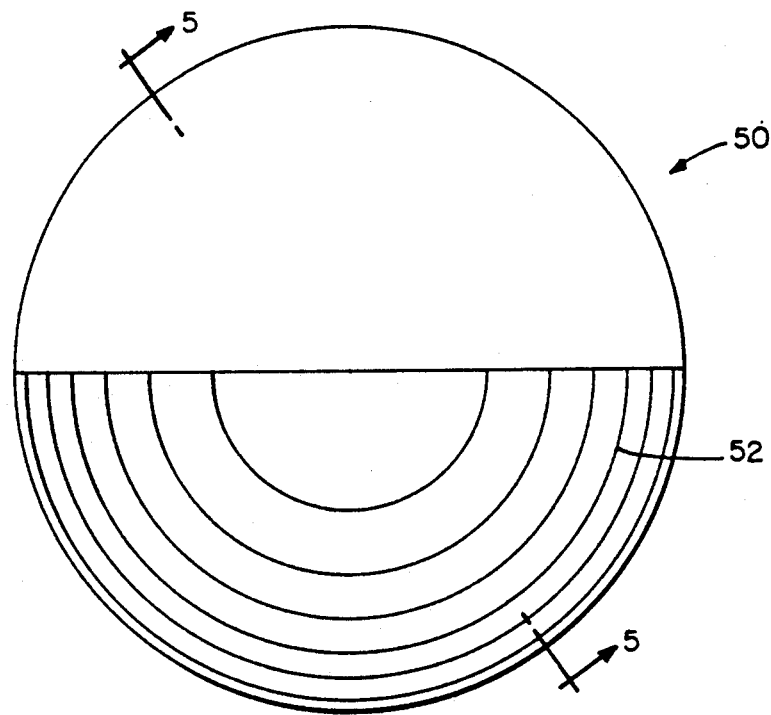
FIG. 4 is a diagram in plan view of the posterior face of an ocular implant according to the invention, on which the diffractive lens profile occupies a semicircular sector.
Figure 5:
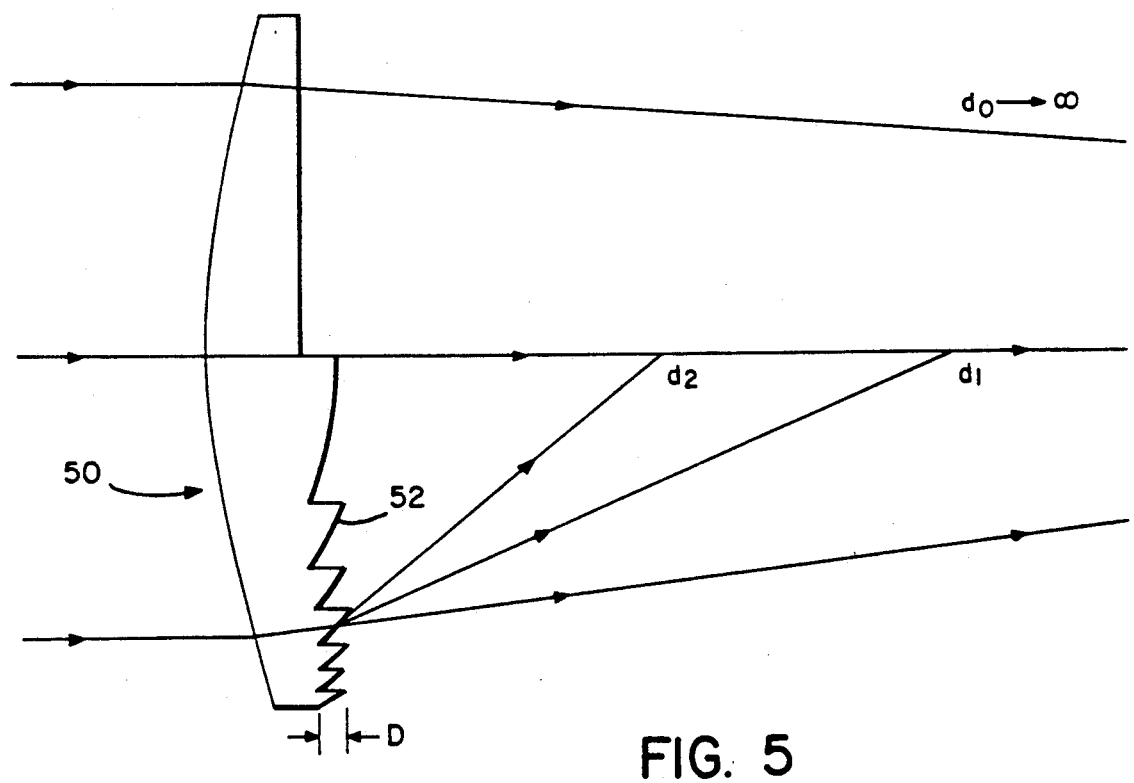
FIG. 5 is a diagram of a section through the optical axis of the intraocular implant of FIG. 4 at 5—5.

Referring now to FIGS. 4 and 5, there is shown a lens 50 is shown having a generally convex-planar configuration and having a "blazed" diffractive lens profile 52 over about half of its posterior surface. The depth D of the diffractive lens profile 52, which is as in FIGS. 2 and 3 exaggerated for illustration, $$D = \frac{\lambda_o}{\Delta n},$$

is such that 100% of the light, of wavelength $\lambda\cdot$, that passes through the diffractive surface is focused in the $d_1$ position. Because the diffractive profile covers only half of the refractive lens surface, this corresponds to 50% of the incident light being focused at $d_1$. The other half of the refractive lens surface has no diffractive component, and light passing through this portion of the lens area "sees" only the refractive lens. This 50% of the incident light will therefore be focused at $d_0$ Such a configuration provides a "bifocal" lens that delivers half the incident light of the given wavelength to each of the two focal positions. Consequently, such a lens can deliver to the retina of the eye in which the lens is implanted a focused image of half the light of the given wavelength from objects within a nearer range and of half the light from objects within a more distant range.

Figure 1:
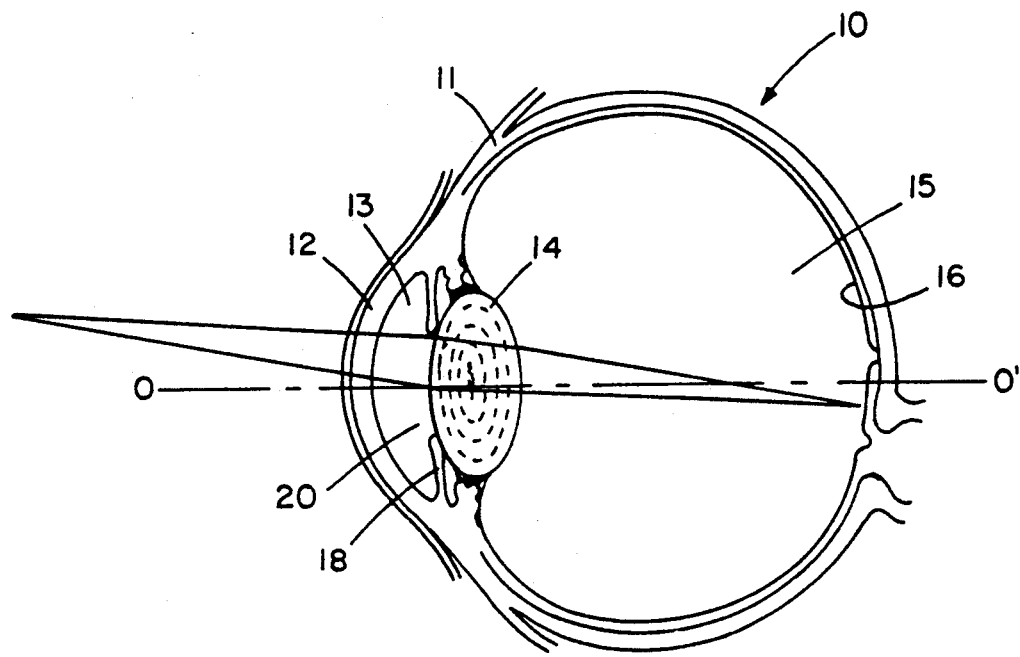
FIG. 1 is a diagram of a human eye showing anatomical features in longitudinal section through the optical axis.
Figure 7:
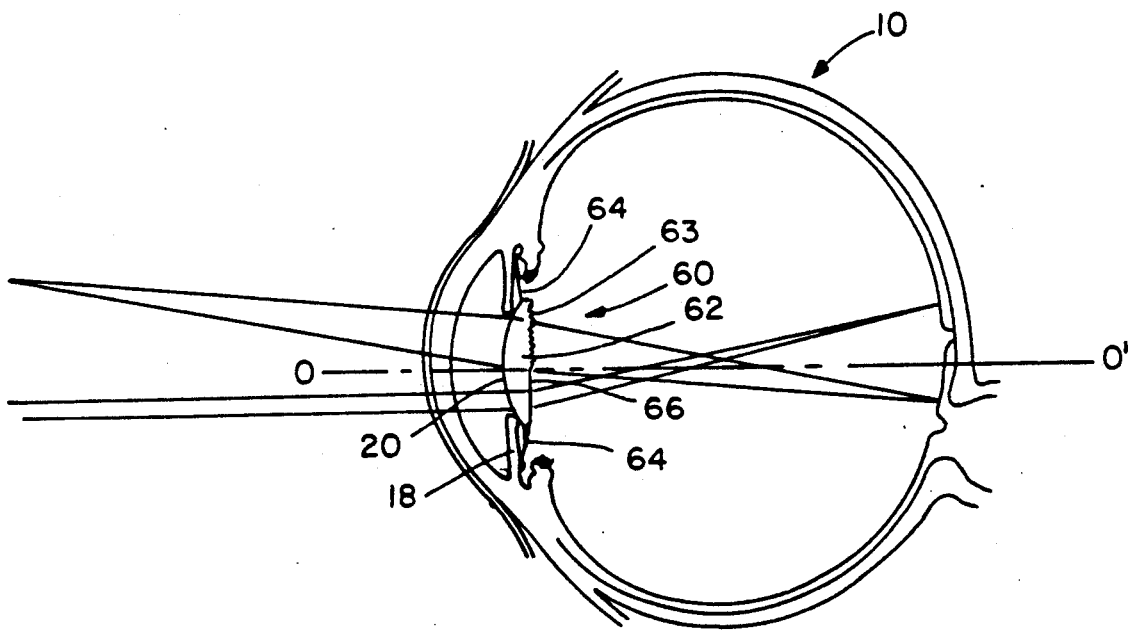
FIG. 7 is a diagram of a human eye as in FIG. 1, in which the natural lens has been replaced with an intraocular implant according to the invention.

FIG. 7 shows by way of example an intraocular lens implant 60 according to the invention implanted in a human eye 10. The implant 60 includes a lens body 62, termed the "optic", on which the refractive/diffractive configuration is formed, and haptics 64, which hold the optic in position behind the iris 18. As the lens body of the intraocular lens implant is very thin, and because the entrance pupil 20 of the eye is located close to the anterior surface 64 of the optic, the posterior surface 66 of the optic, on which the diffractive lens profile 68 is preferably formed, is also very close to the entrance pupil. As a result light entering the eye from any angle will see the same half refractive—half diffractive surface, so long as the optical axis of the lens is near the optical axis O—O' of the eye. Half the light focuses at $d_1$ and half the light focuses at $d_0$ irrespective of incident angle.

A diffractive lens profile having a depth $$D = \frac{\lambda_o}{\Delta n}, \quad (3)$$

as described above is 100% efficient in focusing light at $d_1$ only for wavelength $\lambda\cdot$, and the efficiency is less than 100% at other wavelengths. For proper image formation the important quantity is the product of the diffractive lens efficiency and the wavelength response of the retina, integrated over the visible wavelength region. Mathematically, this is expressed as $$\eta_1 = \frac{1}{\Delta\lambda} \int_{\Delta\lambda} n_1(\lambda) V(\lambda) d\lambda, \quad (4)$$

where $V(\lambda)$ is the retinal wavelength response and $\Delta\lambda$ is the visible wavelength band.

Equation (4) predicts an integrated efficiency of 98% for the above-described diffractive lens operating over the visible region. Therefore, the amount of the total light, incident on the refractive/diffractive lens shown in FIGS. 4 and 5, that is focused at $d_1$ is 49%. The 50% of the incident light that "sees" only the refractive half of the lens is focused at $d_0$. The remaining 1% of the incident light is focused at unwanted $d_m$ locations. This is a substantial improvement over the known refractive/diffractive intraocular lens implant configuration in delivery of useful light to the retina.

Moreover, unlike the known refractive/diffractive intraocular lens implant configuration, the images at $d_0$ and $d_1$ are not pseudo-colored, as performing the integration in equation (4) also shows.

The wavelength at which maximal focussing efficiency occurs can be selected by selecting the depth of the diffractive lens profile according to equation (3). It can be preferable to select a profile depth corresponding to $\lambda\cdot$ at about 550 nm, as that wavelength is in the spectral range of optimal sensitivity for the human visual system. As will be appreciated, other wavelengths can be used, and may be preferred in some circumstances or for some applications.

Figure 6:
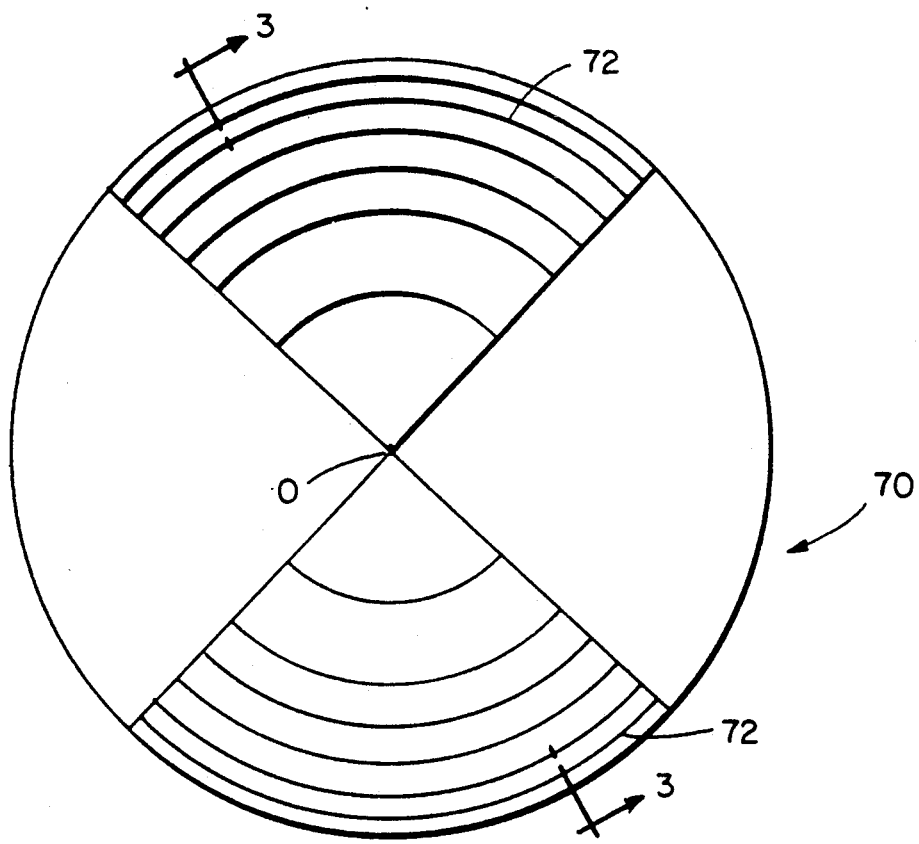
FIG. 6 is a diagram in plan view of the posterior face of an ocular implant according to the invention, on which the diffractive lens profile occupies two quarter-circle sectors.

In even more preferred embodiments the diffractive lens profile occupies a plurality of sectors, the sum of whose subtended angles is 180°. FIG. 6 shows, by way of example, an implant 70 according to the invention having a diffractive lens profile over two quarter-circle sectors 72 oppositely arranged about the optical axis 0 of the lens. Such a configuration can provide coverage of approximately half the effective lens area even when the lens is displaced off-axis with respect to the optical axis of the eye, that is, with respect to the center of the pupil. Circles 74, 76 represent positions of the pupil for off-axis displacements of 10% and 20%, respectively, of the effective lens area, and show that even for 20% displacement close to half the effective lens area is covered by the diffractive lens profile.

FABRICATION

A refractive/diffractive lens as described above with reference to FIG. 4 can be fabricated using a multi-level masking technique, generally described in U.S. Pat. No. 4,895,790, hereby incorporated by reference. As described therein, this fabrication method produces a lens element that can approximate the desired profile shown in FIG. 5 sufficiently well that the amount of incident light focused at $d_1$ is 48%, rather than the theoretical maximum of 49%. The protocol, briefly, is as follows.

Figure 8:
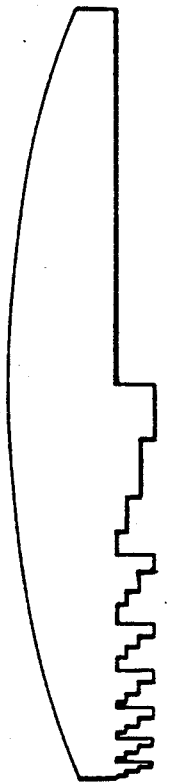
FIG. 8 is a diagram of a section through the optical axis of an intraocular implant having a stepped diffractive lens profile, made using a multi-level masking technique, that approximates the blazed lens profile shown in FIG. 5.

Generally, with reference to FIG. 8, a step profile lens body approximating the blazed profile shown by way of example in FIG. 5, can be made from a material conventionally used in fabricating intraocular implants such as, for example, PMMA, by first for example using the multi-level masking technique to produce a master, then using the master as a plug to form a mold, and then using the mold to form the lens body.

An intraocular lens implant can be made using a lens body having the configuration described above and fabricated by the multi-level masking technique, by providing fixation devices, preferably haptics, as are well known in the art. Or, a one-piece lens having haptics provided as an integral part can be formed using standard fabrication methods combined with the multi-level masking technique.

USE

The overall dimensions and shape of the implant according to the invention are not materially different from those of known intraocular lens implants in common use, and an implant according to the invention can be used instead of or as a replacement for a standard intraocular lens implant using known techniques of intraocular lens implantation.

OTHER EMBODIMENTS

Other embodiments are within the following claims.

I claim:

1. An intraocular optical implant comprising a refractive/diffractive lens having an anterior surface and a posterior surface and a generally anterior-posterior optical axis, at least one of said anterior and posterior surfaces having a diffractive lens profile covering about half the effective lens area of said lens.

2. The implant of claim 1 wherein said diffractive lens profile comprises a Fresnel phase zone plate profile.

3. The implant of claim 2 wherein said diffractive lens profile comprises a blazed diffraction lens profile.

4. The implant of claim 2 wherein said diffractive lens profile comprises a stepped diffractive lens profile.

5. The implant of claim 3 or 4 wherein said diffraction zone profile has a thickness D given by $$D = \frac{\lambda_o}{\Delta n},$$

where $\lambda_o$ is about 550 nm.

6. The implant of claim 1 wherein said diffractive lens profile comprises at least one sectoral portion of said effective lens area.

7. The implant of claim 6 wherein said diffractive lens profile comprises a semicircular sectoral portion of said effective lens area.

8. The implant of claim 6 wherein said diffractive lens profile comprises a plurality of sectoral portions of said effective lens area, the sum of whose subtended angles is about 180°.

9. The implant of claim 8 wherein said diffractive lens profile comprises two sectoral portions of said effective lens area, each of whose subtended angles is about 90°.

* * * * *

UNITED STATES PATENT AND TRADEMARK OFFICE
CERTIFICATE OF CORRECTION

PATENT NO. : 5,089,023
DATED : February 18, 1992
INVENTOR(S) : Gary J. Swanson

It is certified that error appears in the above-indentified patent and that said Letters Patent is hereby corrected as shown below:

Column 5, line 32, delete -- $d_0$Such -- and insert therefor -- $d_0$. Such --.

Column 6, line 18, delete -- refractive/diffractive -- and insert therefor -- refractive/diffractive --; and Signed and Sealed this Fourteenth Day of September, 1993

Attest:

BRUCE LEHMAN

*Attesting Officer*          *Commissioner of Patents and Trademarks*